(12) United States Patent
Shirasawa et al.

(10) Patent No.: US 6,395,932 B1
(45) Date of Patent: May 28, 2002

(54) 1,2-DIPHENYL-2-PROPEN-1-ONE DERIVATIVES

(75) Inventors: Eiichi Shirasawa; Masaki Ichikawa, both of Ikoma; Hiroshi Suhara, Osaka, all of (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/889,140

(22) PCT Filed: Jan. 12, 2000

(86) PCT No.: PCT/JP00/00094

§ 371 (c)(1),
(2), (4) Date: Jan. 12, 2000

(87) PCT Pub. No.: WO00/41993

PCT Pub. Date: Jul. 20, 2000

(30) Foreign Application Priority Data

Jan. 18, 1999 (JP) ............................................. 11-008937

(51) Int. Cl.$^7$ ............................................. C07C 211/00
(52) U.S. Cl. ........................ 564/374; 564/383; 514/654; 514/913
(58) Field of Search ................................. 564/374, 383; 514/649, 654, 913

(56) References Cited

U.S. PATENT DOCUMENTS 4,472,412 A * 9/1984 Buschmann et al.

FOREIGN PATENT DOCUMENTS

| JP | 7-13013 | 12/1987 |
| WO | WO 86/07259 | * 12/1986 |

* cited by examiner

*Primary Examiner*—Samuel Barts
(74) *Attorney, Agent, or Firm*—Frishauf, Holtz, Goodman, Langer & Chick, P.C.

(57) ABSTRACT

The present invention provides compounds represented by the following formula [I] or salts thereof which lower intraocular pressure by causing morphological change in trabecular meshwork cells. In the formula, $R^1$ is H, lower alkyl, hydroxy, lower alkoxy or halogen, $R^2$, $R^3$ and $R^4$ are H or lower alkyl, and ... is a single bond or a double bond. When $R^3$ and/or $R^4$ is hydrogen, the amino can be protected by a protecting group.

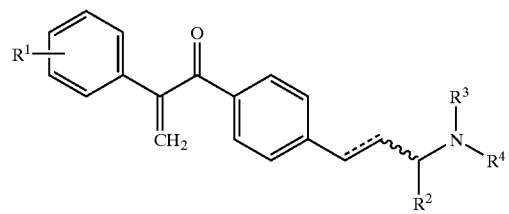

[I]

17 Claims, No Drawings

1,2-DIPHENYL-2-PROPEN-1-ONE DERIVATIVES

This application is a U.S. National Phase application under 35 USC 371 of International Application PCT/JP00/00094 (not published in English) filed Jan. 12, 2000.

TECHNICAL FIELD

The present invention relates to novel compounds which are useful as therapeutic agents for glaucoma.

BACKGROUND ART

In general, glaucoma is a disease wherein visual functions suffer disorders caused by a rise of intraocular pressure. Aqueous humor outflow is closely related to the rise of intraocular pressure. When the aqueous humor outflow is disturbed, the intraocular pressure rises. The aqueous humor flows mainly from trabecular meshwork through a Schlemm's canal outside an eyeball. The aqueous humor outflow can be increased by reducing resistance of the aqueous humor outflow in this trabecular meshwork. Cells which form the trabecular meshwork (trabecular meshwork cells) have sulfhydryl groups. A method of lowering the intraocular pressure has been reported, in which a compound capable of reacting with the sulfhydryl groups is administered so as to make a morphological change in the trabecular meshwork cells and increase the rate of aqueous humor outflow. (Japanese Examined Patent Publication No. 13013/1995). This patent Publication discloses phenoxyacetic acid derivatives, preferably ethacrynic acid as compounds capable of reacting with the sulfhydryl groups.

The method of lowering the intraocular pressure by causing the morphological change in the trabecular meshwork cells is very interesting as a method of treating glaucoma. However, there have not been so many studies of drugs having such a function mechanism yet. A study of creating new drugs in development of therapeutic agents for glaucoma is a very interesting subject.

DISCLOSURE OF THE INVENTION

Accordingly, noting that ethacrynic acid, which is a phenoxyacetic acid derivative having an α,β-unsaturated carbonyl group, has an effect of causing the morphological change in the trabecular meshwork cells and lowering the intraocular pressure, the present inventors synthesized various novel compounds and studied their effects on morphology of the trabecular meshwork cells. As a result, the present inventors found that novel 1,2-diphenyl-2-propen-1-one derivatives, that is, compounds having a 1,2-diphenyl-2-propen-1-one structure as a basic structure and an amino group introduced into their side chain of the benzene ring at the 1st-position, have excellent effects. Thus, the present invention has been completed.

The present invention relates to compounds represented by the following general formula [I] and salts thereof (hereinafter referred to as "the present compound" as far as there is no proviso), and pharmaceutical compositions containing them as active ingredients:

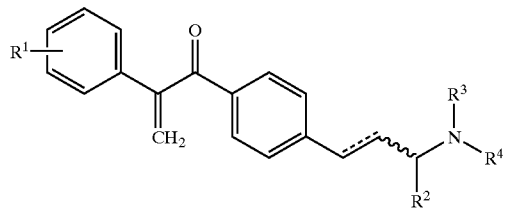

wherein $R^1$ is hydrogen, lower alkyl, hydroxy, lower alkoxy or halogen, $R^2$, $R^3$ and $R^4$, being the same or different, are hydrogen or lower alkyl, and ⋯ is a single bond or a double bond.

The groups defined above are described in detail hereinafter.

The lower alkyl is straight-chain or branched alkyl having one to eight carbon atoms such as methyl, ethyl, propyl, butyl, hexyl, isopropyl, isobutyl, isopentyl, isohexyl, t-butyl or 3,3-dimethylbutyl.

The lower alkoxy is straight-chain or branched alkoxy having one to eight carbon atoms such as methoxy, ethoxy, propoxy, butoxy, hexyloxy, isopropoxy or t-butoxy.

The halogen is fluorine, chlorine, bromine or iodine.

When $R^3$ and/or $R^4$ is hydrogen in the present compounds, the amino group can be protected by a protecting group. The protecting group of the amino group is a general protecting group of an amino group such as acyl, ester, substituted lower alkyl or substituted sulfonyl. In detail, examples of the protecting group are acyl such as formyl, lower alkanoyl, halogeno-lower alkanoyl or phenylcarbonyl; ester such as lower alkoxycarbonyl, substituted lower alkoxycarbonyl or phenoxycarbonyl; substituted lower alkyl such as allyl, phenyl-lower alkyl or benzoyl-lower alkyl; and substituted sulfonyl such as lower alkylsulfonyl or phenylsulfonyl. Each phenyl ring of the above-mentioned phenylcarbonyl, phenoxycarbonyl, phenyl-lower alkyl, benzoyl-lower alkyl and phenylsulfonyl can be substituted by halogen, lower alkyl, lower alkoxy or nitro.

Specific examples of preferred protecting groups of the amino group are acyl such as formyl, acetyl, trichloroacetyl, trifluoroacetyl or benzoyl; ester such as methoxycarbonyl, isobutoxycarbonyl, t-butoxycarbonyl, allyloxycarbonyl, 2,2,2-trichloroethoxycarbonyl, benzyloxycarbonyl, diphenylmethoxycarbonyl or phenoxycarbonyl; substituted alkyl such as allyl, benzyl, trityl or (4-methoxyphenyl)diphenylmethyl; and substituted sulfonyl such as benzenesulfonyl, 2,4,6-trimethylbenzenesulfonyl or toluenesulfonyl.

When $R^1$ is hydroxy, the hydroxy can be protected by a general protecting group similarly to amino protection.

Salts in the present invention refer to any pharmaceutically acceptable salts and are exemplified by salts with an inorganic acid such as hydrochloric acid, nitric acid or sulfuric acid, salts with an organic acid such as acetic acid, fumaric acid, maleic acid, citric acid or tartaric acid and the like. When there are geometrical isomers or optical isomers in the present compounds, these isomers are also included in the present invention.

The present compounds can be in the form of solvates such as hydrates.

Preferred examples of the present compound are compounds wherein the group(s) is (are) the followings in the compounds represented by the general formula [I] or salts thereof, (1a) $R^1$ is a group selected from hydrogen, lower alkyl and halogen; and/or (2a) $R^2$ is hydrogen; and/or (3a) both $R^3$ and $R^4$ are lower alkyl.

Namely,

Compounds defined by above (1a) in the compounds represented by the general formula [I] or salts thereof, Compounds defined by above (2a) in the compounds represented by the general formula [I] or salts thereof, Compounds defined by above (3a) in the compounds represented by the general formula [I] or salts thereof, and Compounds defined by any combinations of two or more of above (1a), (2a) and (3a) in the compounds represented by the general formula [I] or salts thereof.

The most preferred examples of the present compound are the following compounds and salts thereof.

1) 1-[4-[(E)-3-(Dimethylamino)-1-propenyl]phenyl-2-phenyl-2-propen-1-one

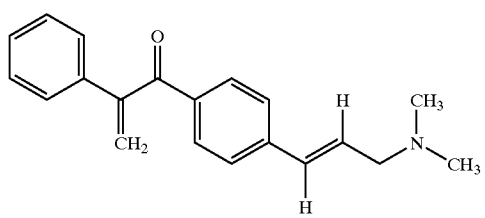

2) 1-[4-[3-(Dimethylamino)propyl]phenyl-2-phenyl-2-propen-1-one

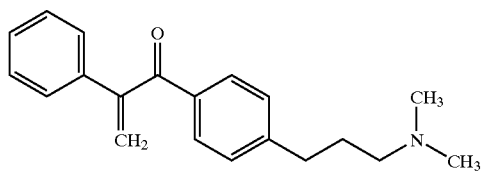

The present invention also relates to compounds represented by the following general formula [IV], which are synthetic intermediates of the compounds represented by the above general formula [I], and salts thereof:

[IV]

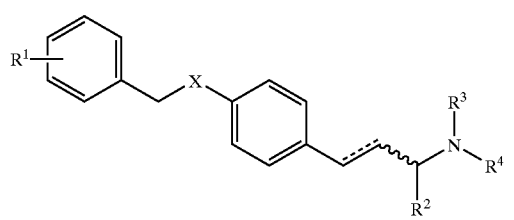

wherein $R^1$, $R^2$, $R^3$, $R^4$ and ⋯ have the same definitions as mentioned above, and >X is >CHOH or >C=O. When $R^3$ and/or $R^4$ is hydrogen, the amino group can be protected by protecting group(s).

A typical synthetic route of the present compound [I] is shown below.

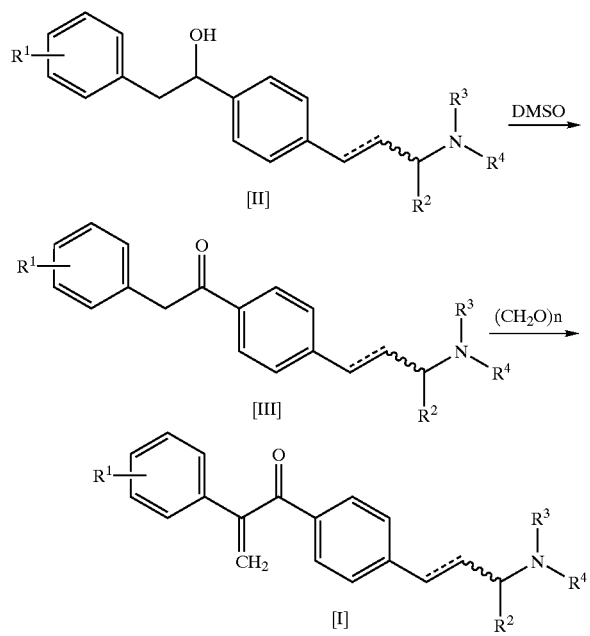

The above synthetic route does not represent all methods, but one typical example. Details of specific synthetic methods are described in later Examples.

A synthetic method of the above route is described in detail below.

The aminoalcohol [II] (compound wherein >X is >CHOH in the compound represented by the general formula [IV] and salts thereof) is treated in the presence of an Oxidizing agent (for example, dimethyl sulfoxide (DMSO)) to give the carbonyl compound represented by the formula [III] (compound wherein >X is >C=O in the compound represented by the general formula [IV] and salts thereof). Next, the compound [III] is condensed with paraformaldehyde in the presence of a secondary amine by Mannich reaction, and then the present compound [I] is obtained by elimination reaction.

When the reactants have a hydroxy group or an amino group in their molecule in the above-mentioned synthetic method, the group can be protected optionally by a suitable protecting group, and the protecting group can also be removed by a conventional method after the reaction.

The present compounds are novel compounds which are unknown in literatures, and are characterized in that the present compounds have a 1,2-diphenyl-2-propen-1-one structure, that is, the compounds have an α,β-unsaturated carbonyl group substituted by two benzene rings, as a basic structure, and an amino group is introduced into a side chain of the benzene ring at the 1st-position.

As described above in the section of "Background Art", it was reported that ethacrynic acid has an effect of lowering intraocular pressure by making a morphological change in trabecular meshwork cells and increasing the rate of aqueous humor outflow (see Japanese Examined Patent Publication No. 13013/1995). Ethacrynic acid is a phenoxyacetic acid derivative having an α,β-unsaturated carbonyl group. Focusing attention on this chemical structure of ethacrynic acid, the present inventors studied precisely and found that novel compounds exhibiting higher effects are obtained by introducing one benzene ring into the α-position of ethacrynic acid and by further introducing an amino group into the side chain of the other benzene ring.

Administration methods of drugs can be a method of administering active compounds themselves or a method of administering the drugs in the form to be decomposed in vivo and to be converted into the active compounds, namely in the form of prodrugs. Both are widely used. When the present compounds have a hydroxy group or an amino group protected by a suitable protecting group in their molecules, the present compounds can be administered with the hydroxy group or the amino group protected by the protecting group. The present compounds can also be administered after removing the protecting group to convert the protected group into the hydroxy group or the amino group.

In order to study utility of the present compounds, effects of the present compounds on morphology of the trabecular meshwork cells were investigated. Details will be described later in the section of "Pharmacological Test", and morphological changes of the trabecular meshwork cells by adding the present compounds were studied by image analysis. As a result, the present compounds exhibited excellent cell morphology change effects on the trabecular meshwork cells. Accordingly, the present compounds are considered to have excellent intraocular pressure-lowering effects.

The present compound is mainly administered parenterally and can also be administered orally. Examples of dosage forms are eyedrops, injections, tablets, capsules, granules and the like. The present compound can be formulated into preparations by conventional methods. For example, eyedrops can be prepared by optionally using an isotonic agent such as sodium chloride or concentrated glycerine; a buffer such as sodium phosphate or sodium acetate; a surfactant such as polyoxyethylenesorbitan monooleate, polyoxyl 40 stearate or polyoxyethylene hydrogenated castor oil; a stabilizer such as sodium citrate or disodium edetate; a preservative such as benzalkonium chloride or paraben; or the like. pH can be in a range acceptable for ophthalmic preparations, and it is preferably in a range of 4 to 8. Oral preparations such as tablets, capsules and granules can be prepared by optionally using a diluent such as lactose, starch, crystalline cellulose or vegetable oil; a lubricant such as magnesium stearate or talc; a binder such as hydroxypropylcellulose or polyvinyl pyrrolidone; a disintegrator such as calcium carboxymethylcellulose; a coating agent such as hydroxypropylmethylcellulose, macrogol or silicone resin; or a gelatin film-forming agent.

The dosage of the present compound can be selected suitably depending on symptoms, age, dosage form and the like. In the case of eyedrops, they are instilled once to several times per day with a concentration of 0.001 to 3% (w/v) solution. In the case of oral preparations, the usual daily dosage is 1 to 1000 mg, which can be given in a single dose or several divided doses.

Preparations, formulations and results of pharmacological test of the present compounds are shown below. These examples do not limit the scope of the present invention, but are intended to make the present invention more clearly understandable.

BEST MODE FOR CARRYING OUT THE INVENTION

PREPARATION COMPOUNDS

REFERENCE EXAMPLE 1

4-(Phenylacetyl)cinnamic Acid (Reference compound No. 1-1)

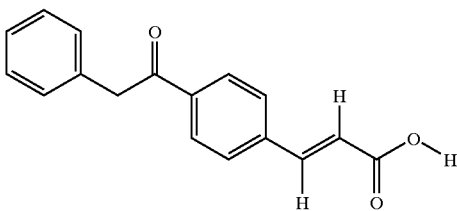

1) Thionyl chloride (3.3 ml) is added dropwise to a solution of ethyl 4-carboxycinnamate (2.0 g) in chloroform (4 ml) under a nitrogen atmosphere, then dimethylformamide (one drop) is added thereto, and the mixture is refluxed for 30 minutes. The reaction mixture is concentrated under reduced pressure to give a residue of corresponding acid chloride. The residue is dissolved in tetrahydrofuran (30 ml) under a nitrogen atmosphere, and the solution is cooled with dry ice. A 2.0 M solution of benzylmagnesium chloride in tetrahydrofuran (4.5 ml) is added dropwise thereto. Twelve minutes after completing the addition, a 10% aqueous citric acid solution is added to the reaction mixture under dry ice cooling, then the temperature is raised to room temperature, and the whole is extracted with ether. The organic layer is washed with water and saturated brine successively, dried over anhydrous magnesium sulfate and concentrated under reduced pressure. The resulting residue is purified by silica gel column chromatography to give ethyl 4-(phenylacetyl) cinnamate (675 mg) as crystals.

mp 110.5~111.3° C.; IR (KBr, cm$^{-1}$) 2986, 1690, 1410, 1330, 1206, 970, 704.

2) A 1 N aqueous sodium hydroxide solution (2.3 ml) and water (4 ml) are added to a solution of ethyl 4-(phenylacetyl) cinnamate (675 mg) in ethanol (6 ml)-tetrahydrofuran (6 ml) under a nitrogen atomosphere, and the mixture is stirred at room temperature for 6.5 hours. To the reaction mixture is added 1 N hydrochloric acid to acidify it, and the whole is extracted with ethyl acetate. The organic layer is washed with saturated brine, dried over anhydrous magnesium sulfate and concentrated under reduced pressure. The resulting precipitates are filtered off to give the titled compound (Reference compound No. 1-1) as crystals.

(Reference compound No. 1-1)

mp 232~236° C. (decomp.); IR (KBr, cm$^{-1}$) 3036, 2589, 1684, 1630, 1337, 1230, 993.

The following compounds are obtained by a method similar to Reference Example 1.

4-[(4-Tolyl)acetyl]cinnamic acid (Reference compound No. 1-2)

4-[(4-Fluorophenyl)acetyl]cinnamic acid (Reference compound No.1-3)

4-[(4-Chlorophenyl)acetyl]cinnamic acid (Reference compound No. 1-4)

REFERENCE EXAMPLE 2

3-[4-(Phenylacetyl)phenyl]propionic Acid (Reference compound No. 2-1)

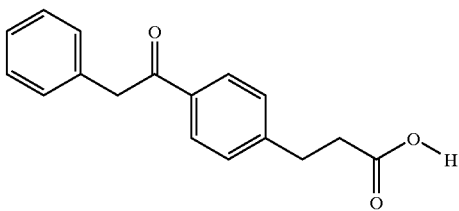

1) Phenylacetyl chloride (3.4 ml) is added to a solution of anhydrous aluminum chloride (4.27 g) in 1,2-dichloroethane (35 ml) under ice cooling, and then a solution of ethyl 3-phenylpropionate (5.1 g) in anhydrous 1,2-dichloroethane (5 ml) is added dropwise thereto. The mixture is stirred under ice cooling for 20 minutes and at room temperature overnight. The reaction mixture is added little by little to a saturated aqueous sodium hydrogencarbonate solution (150 ml) containing ice (100 g). The resulting precipitates are filtered out. Ether is added to the filtrate. The organic layer is washed with a saturated aqueous sodium hydrogencarbonate solution and saturated brine successively, dried over anhydrous magnesium sulfate and concentrated under reduced pressure. The resulting residue is purified by silica gel column chromatography to give ethyl 3-[4-(phenylacetyl)phenyl]propionate as crystals.

mp 50.5~52.5° C.; IR (KBr, cm$^{-1}$) 3059, 2977, 2921, 1735, 1682, 1605, 1479, 1455, 1437, 1357, 1316, 1181, 822.

2) A 1 N aqueous sodium hydroxide solution (3.1 ml) is added to a solution of ethyl 3-[4-(phenylacetyl)phenyl] propionate (700 mg) in ethanol (6 ml)-tetrahydrofuran (3 ml), and the mixture is stirred at room temperature for two hours. A 10% aqueous citric acid solution is added to the reaction mixture to acidify it, and the whole is extracted with ethyl acetate. The organic layer is washed with water and saturated brine successively, dried over anhydrous sodium sulfate and concentrated under reduced pressure. The resulting precipitates are filtered off to give the titled compound (Reference compound No. 2-1) as crystals.
(Reference compound No. 2-1)

mp 132~137° C. IR (KBr, cm$^{-1}$) 3497, 3028, 1680, 1607, 1498, 1455, 1348, 1221, 1182, 992, 826.

REFERENCE EXAMPLE 3

N,N-Dimethyl-4-(phenylacetyl)cinnamamide (Reference compound No. 3-1)

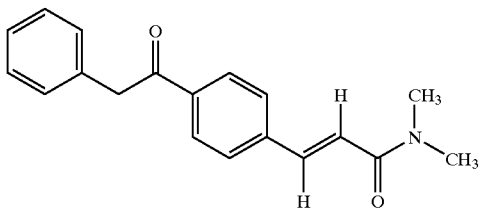

To a solution of 4-(phenylacetyl)cinnamic acid (Reference compound No. 1-1, 3.23 g) in anhydrous tetrahydrofuran (120 ml) chloroform (20 ml) are added 1-hydroxybenzotriazole (1.64 g), dimethylamine hydrochloride (1.19 g), N-methylmorpholine (3.1 ml) and 1-ethyl-3-(3-dimethylaminopropyl)carbodiimide hydrochloride (2.56 g), and the mixture is stirred at room temperature for five hours. The reaction mixture is concentrated under reduced pressure, a 10% aqueous citric acid solution is added to the concentrate, and the whole is extracted with ethyl acetate. The organic layer is washed with water, a saturated aqueous sodium hydrogencarbonate solution, water and saturated brine successively, dried over anhydrous magnesium sulfonate and concentrated under reduced pressure. The resulting precipitates are filtered off to give the titled compound (Reference compound No. 3-1, 3.00 g) as crystals.
(Reference compound No. 3-1)

mp 138.5~141.5 ° C.; IR (KBr, cm$^{-1}$) 3030, 1684, 1653, 1604, 1498,1413, 1328, 1205, 992, 967.

The following compounds are obtained by a method similar to Reference Example 3.

N,N-Dimethyl-3-[4-(phenylacetyl)phenyl]propionamide (Reference compound No. 3-2)

mp 125~131 ° C.; IR (KBr, cm$^{-1}$) 3028, 2908, 1684, 1640, 1604, 1495, 1452, 1407, 1141.

N,N-Dimethyl-4-[(4-tolyl)acetyl]cinnamamide (Reference compound No. 3-3)

N,N-Dimethyl-4-[(4-fluorophenyl)acetyl]cinnamamide (Reference compound No. 3-4)

4-[(4-Chlorophenyl)acetyl]-N,N-dimethylcinnamamide (Reference compound No. 3-5)

4-(Phenylacetyl)cinnamamide (Reference compound No. 3-6)

EXAMPLE 1

1-[4-[(E)-3 -(Dimethylamino)-1-propenyl]phenyl]-2-phenyl-1-ethanol Hydrochloride (Compound No. 1-1)

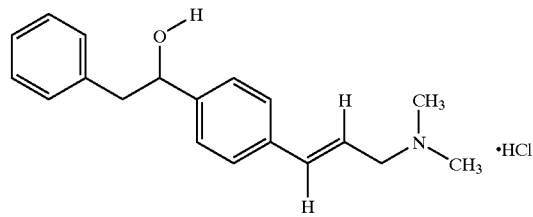

A solution of N,N-dimethyl-4-(phenylacetyl) cinnamamide (Reference compound No. 3-1, 3.00 g) in anhydrous tetrahydrofuran (72 ml) is added dropwise to a suspension of lithium aluminum hydride (0.58 g) in anhydrous tetrahydrofuran (30 ml) under ice cooling and a nitrogen atmosphere. After completing the addition, the mixture is stirred at room temperature for 20 minutes.

Anhydrous sodium sulfate is added to the reaction mixture, and water is added dropwise thereto with stirring. The resulting insoluble matter is filtered out, and the filtrate is concentrated under reduced pressure. The resulting residue is purified by silica gel column chromatography and dissolved in a 4.0 N solution of hydrogen chloride in ethyl acetate. After vacuum concentration, the resulting precipitates are filtered off to give the titled compound (Compound No. 1-1, 0.80 g) as crystals.
(Compound No. 1-1)

mp 152~164° C.; IR (KBr, cm$^{-1)}$ 3334, 2954, 2664, 1650, 1418, 1161, 1034, 984, 752, 708.

The following compounds are obtained by a method similar to Example 1.

1-[4-[3-(Dimethylamino)propyl]phenyl]-2-phenyl-1-ethanol (Compound No. 1-2)

IR (Film, cm$^{-1}$) 3026, 2941, 2860, 2778, 1495, 1454, 1042.

1-[4-[(E)-3-(Dimethylamino)-1-propenyl]phenyl]-2-(4-tolyl)-1-ethanol (Compound No. 1-3)

1-[4-[(E)-3-(Dimethylamino)-1-propenyl]phenyl]-2-(4-fluorophenyl)-1-ethanol (Compound No. 1-4)

2-(4-Chlorophenyl)-1-[4-[(E)-3-(dimethylamino)-1-propenyl]phenyl]-1-ethanol (Compound No. 1-5)

1-[4-[(E)-3-Amino-1-propenyl]phenyl]-2-phenyl-1-ethanol (Compound No. 1-6).

EXAMPLE 2
1-[4-[(E)-3-(Acetylamino)-1-propenyl]phenyl]-2-phenyl-1-ethanol (Compound No. 2-1)

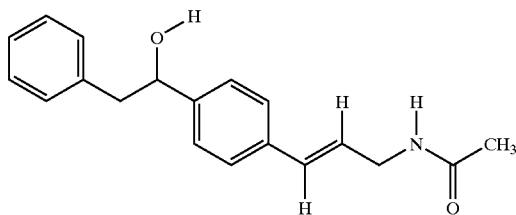

1-[4-[(E)-3-Amino-1-propenyl]phenyl]-2-phenyl-1-ethanol (Compound No. 1-6) is treated with acetic anhydride in pyridine to give the titled compound (Compound No. 2-1).

EXAMPLE 3
1-[4-[(E)-3-(Dimethylamino)-1-propenyl]phenyl]-2-phenyl-1-ethanone (Compound No. 3-1)

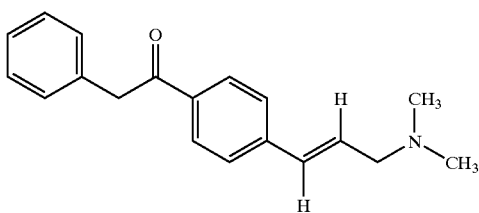

Triethylamine (2.1 ml) is added to a solution of 1-[4-[(E)-3-(dimethylamino)-1-propenyl]phenyl]-2-phenyl-1-ethanol hydrochloride (Compound No. 1-1, 800 mg) in dimethyl sulfoxide (15 ml) at room temperature with stirring, and further a solution of a sulfur trioxide-pyridine complex (1.6 g) in dimethyl sulfoxide (10 ml) is added dropwise thereto. The mixture is stirred at room temperature for three hours, a 0.1 N aqueous sodium hydroxide solution is added to the reaction mixture, and the whole is extracted with ether. The organic layer is washed with saturated brine, dried over anhydrous magnesium sulfate and concentrated under reduced pressure. The resulting residue is purified by silica gel column chromatography to give the titled compound (Compound No. 3-1, 270 mg) as crystals.

(Compound No. 3-1)

IR (KBr, cm$^1$) 2767, 1682, 1599, 1452, 1408, 1332, 1219, 1175, 975, 726, 697.

The following compounds are obtained by a method similar to Example 3.

1-[4-[3-(Dimethylamino)propyl]phenyl]-2-phenyl-1-ethanone (Compound No. 3-2)

mp 37.8~40.0 ° C.; IR (KBr, cm$^{-1)}$ 2809, 2758, 1682, 1601, 1565, 1493, 1453, 1409.

1-[4-[(E)-3-(Dimethylamino)-1-propenyl]phenyl]-2-(4-tolyl)-1-ethanone (Compound No. 3-3)

1-(4-[(E)-3-(Dimethylamino)-1-propenyl]phenyl]-2-(4-fluorophenyl)-1-ethanone (Compound No. 3-4)

2-(4-Chlorophenyl)-1-[4-[(E)-3-(dimethylamino)-1-propenyl]phenyl]-1-ethanone (Compound No. 3-5)

1-[4-[(E)-3-(Acetylamino)-1-propenyl]phenyl]-2-phenyl-1-ethanone (Compound No. 3-6).

EXAMPLE 4
1-[4-[(E)-3-(Dimethylamino)-1-propenyl]phenyl]-2-phenyl-2-propen-1-one (Compound No. 4-1)

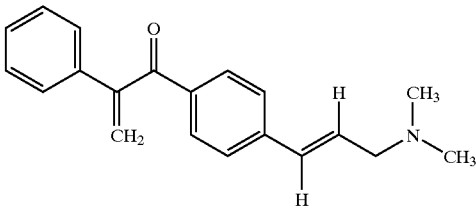

A solution of 1-[4-[(E)-3-(dimethylamino)-1-propenyl]phenyl]-2-phenyl-1-ethanone (Compound No. 3-1, 200 mg) in dioxane (10 ml) is introduced into a pressure tube. To the solution are added paraformaldehyde (86 mg), dimethylamine hydrochloride (233 mg), acetic acid (one drop) and anhydrous magnesium sulfate (1 g), and the whole is stirred overnight while heating it at 120° C. A saturated aqueous sodium hydrogencarbonate solution is added to the reaction mixture under ice cooling to basify it, and the whole is extracted with ethyl acetate. The organic layer is washed with saturated brine, dried over anhydrous magnesium sulfate and concentrated under reduced pressure. The resulting residue is purified by silica gel column chromatography to give the titled compound (Compound No. 4-1, 145 mg).

(Compound No. 4-1)

IR (Film, cm$^{-1}$) 2941, 2771, 1664, 1601, 1412, 1217, 1175, 980, 700.

The following compounds are obtained by a method similar to

EXAMPLE 4

1-[4-[3-(Dimethylamino)propyl]phenyl]-2-phenyl-2-propen-1-one (Compound No. 4-2)

IR (KBr, cm$^{-1}$) 3416, 3027, 2942, 2814, 2765, 1665, 1604, 1465, 1415, 981, 915.

1-[4-[(E)-3-(Dimethylamino)-1-propenyl]phenyl]-2-(4-tolyl)-2-propen-1-one (Compound No. 4-3)

1-[4-[(E)-3-(Dimethylamino)-1-propenyl]phenyl]-2-(4-fluorophenyl)-2-propen-1-one (Compound No. 4-4)

2-(4-Chlorophenyl)-1-[4-[(E)-3-(dimethylamino)-1-propenyl]phenyl]-2-propen-1-one (Compound No. 4-5)

1-[4-[(E)-3-(Acetylamino)-1-propenyl]phenyl]-2-phenyl-2-propen-1-one (Compound No. 4-6).

Formulation

Formulation examples of eyedrops and oral preparation using the present compound are shown below.

| 1) Eyedrops | |
|---|---|
| In 10 ml | |
| Present compound | 1 mg |
| Concentrated glycerin | 250 mg |
| Polysorbate 80 | 200 mg |
| Sodium dihydrogenphosphate dihydrate | 20 mg |
| 1N Sodium hydroxide | q.s. |
| 1N Hydrochloric acid | q.s. |
| Sterile purified water | q.s. |

-continued

2) Tablet

In 100 mg

| Present compound | 1 mg |
|---|---|
| Lactose | 66.4 mg |
| Cornstarch | 20 mg |
| Calcium carboxymethylcellulose | 6 mg |
| Hydroxypropylcellulose | 6 mg |
| Magnesium stearate | 0.6 mg |

Pharmacological Test

In order to study utility of the present compounds in glaucoma, effects of the present compounds on morphology of trabecular meshwork cells were investigated.

1) Effects on Morphology of Trabecular Meshwork Cells

The possibility has been reported that drugs having effects of increasing aqueous humor outflow can be found by evaluating effects of drugs on morphology of cultured trabecular meshwork cells (Invest. Ophthalmol. Vis. Sci., 33, 2631–2640 (1992)). Accordingly, effects of the present compounds on morphology of bovine cultured trabecular meshwork cells were studied in the similar manner to the method described in the above-mentioned literature.

Experimental Method

Morphological changes in bovine cultured trabecular meshwork cells by adding the present compounds were quantitatively evaluated by image analysis.

Preparation of Cells

Bovine trabecular meshwork cells (passage number 2 to 5) cultured in a basal medium for mammalian cell culture D-MEM (Dulbecco's Modified Eagle Medium, manufactured by Gibco Co., Ltd.) containing fetal bovine serum (10%), amphotericin B (2.5 μg/ml) and gentamicin (50 μg/ml) were treated with a trypsin-EDTA solution (0.05% trypsin, 0.53 mM EDTA·4Na) 24 hours before the later drug treatment and seeded in a 24-well plate ($10^4$ cells/well). Twelve hours before the later drug treatment, the cells were washed with phosphate-buffered physiological saline, and then the medium was replaced by D-MEM containing amphotericin B (2.5 μg/ml) and gentamicin (50 μg/ml) (hereinafter referred to as "medium A"). One hour before the later drug treatment, cells which did not contact each other were selected from the cells prepared as mentioned above and used for experiment.

Preparation of Test Compound Solution

A test compound was dissolved in dimethyl sulfoxide (DMSO), and the medium A was added to the solution, followed by sterilizing the solution by filtration. The medium A was further added to the solution to dilute it at a prescribed concentration. This diluted solution was maintained isothermally under a 5% carbon dioxide gas atmosphere at 37° C. for one hour, from one hour before the later drug treatment to prepare a test compound solution.

Method of Measurement

First, cells were photographed using a well-scanner one hour before the drug treatment. Next, the medium of the cells was replaced by the test compound solution, and the cells were treated with the drug and incubated under a 5% carbon dioxide gas atmosphere at 37° C. for three hours. Then, the same cells as those photographed one hour before the drug treatment were photographed using the well-scanner.

Image Analysis

Photographed cell images were incorporated from the photographs into an image analysis system with a CCD camera (manufactured by HAMAMATU Co., Ltd.). Outlines of the incorporated cell images were traced, and areas were measured. Degrees of the morphological changes made by the test compounds on the trabecular meshwork cells are expressed by the following rates of changes in areas (%).

Rate of change in area (%)=[(A-B)/A]×100

A: Cell area before drug treatment
B: Cell area after drug treatment

Results

Table 1 shows concentrations required to reduce the cell area of the trabecular meshwork cells by 50%, i.e., $EC_{50}$, as examples of test results. Table 1 shows also a result using ethacrynic acid as a control drug.

TABLE 1

| Test compound | $EC_{50}$ (M) |
|---|---|
| Compound No. 4-1 | $5.8 \times 10^{-7}$ |
| Compound No. 4-2 | $8.4 \times 10^{-7}$ |
| Ethacrynic acid | $6.2 \times 10^{-5}$ |

Table 1 shows that the present compounds have excellent cell morphological change effects on the trabecular meshwork cells. These effects were much higher than that of ethacrynic acid, which was a known comparative control drug.

The above-mentioned results show that the present compounds. have the excellent cell morphological change effects and are useful as intraocular pressure-lowering agents, namely therapeutic agents for glaucoma.

Industrial Applicability

The present invention provides compounds which lower intraocular pressure by causing morphological change in trabecular meshwork cells. These compounds are useful as therapeutic agents for glaucoma.

What is claimed is:

1. A compound represented by the following formula or a salt thereof,

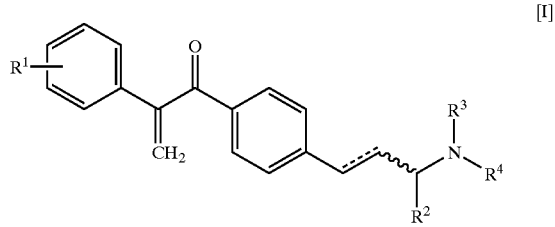

wherein $R^1$ is hydrogen, lower alkyl, hydroxy, lower alkoxy or halogen, $R^2$, $R^3$ and $R^4$ are the same or different and are hydrogen or lower alkyl, and ... is a single bond or a double bond.

2. The compound or a salt thereof as claimed in claim 1, wherein $R^3$ and/or $R^4$ is hydrogen, and the amino group is protected by a protecting group.

3. The compound or a salt thereof as claimed in claim 1, wherein $R^1$ is a group selected from hydrogen, lower alkyl and halogen.

4. A compound or a salt thereof as claimed in claim 1, wherein the compound is 1-[4-[(E)-3-(dimethylamino)-1-propenyl]phenyl-2-phenyl-2-propen-1-one.

5. A pharmaceutical composition comprising a pharmaceutically effective amount of the compound or a salt thereof as claimed in claim 1 as an active ingredient in combination with a pharmacologically acceptable carrier.

6. A method for improving aqueous humor outflow in a patient comprising administering to a patient a pharmaceutically effective amount of the compound or a salt thereof as claimed in claim 1 as an active ingredient.

7. A method for lowering intraocular pressure in a patient comprising administering to a patient a pharmaceutically effective amount of the compound or a salt thereof as claimed in claim 1 as an active ingredient.

8. A compound represented by the following formula or a salt thereof,

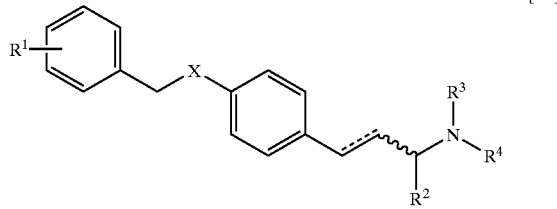

[IV]

wherein $R^1$ is hydrogen, lower alkyl, hydroxy, lower alkoxy or halogen, $R^2$, $R^3$ and $R^4$ are the same or different and are hydrogen or lower alkyl, ⋯ is a single bond or a double bond, >X is >CHOH or >C=O, and when $R^3$ and/or $R^4$ is hydrogen, the amino group is unprotected or protected by a protecting group.

9. The compound or a salt thereof as claimed in claim 1, wherein $R^2$ is hydrogen.

10. The compound or a salt thereof as claimed in claim 3, wherein $R^2$ is hydrogen.

11. The compound or a salt thereof as claimed in claim 1, wherein both $R^3$ and $R^4$ are lower alkyl.

12. The compound or a salt thereof as claimed in claim 3, wherein both $R^3$ and $R^4$ are lower alkyl.

13. The compound or a salt thereof as claimed in claim 10, wherein both $R^3$ and $R^4$ are lower alkyl.

14. The compound or a salt thereof as claimed in claim 1, wherein the compound is 1-[4-[3-(dimethylamino)propyl] phenyl-2-phenyl-2-propen-1-one.

15. The method as claimed in claim 6, wherein the compound is selected from the group consisting of 1-[4-[(E)-3-(dimethylamino)-1-propenyl]phenyl-2-phenyl-2-propen-1-one and 1-[4-[3-(dimethylamino)propyl]phenyl-2-phenyl-2-propen-1-one.

16. The method as claimed in claim 7, wherein the compound is selected from the group consisting of 1-[4-[(E)-3-(dimethylamino)-1-propenyl]phenyl-2-phenyl-2-propen-1-one and-1-4-[13-(dimethylamino)propyl]phenyl-2-phenyl-2-propen-1-one.

17. The composition as claimed in claim 5, wherein the compound is selected from the group consisting of 1-[4-[(E)-3-(dimethylamino)-1-propenyl]phenyl-2-phenyl-2-propen-1-one and 1-[4-[3-(dimethylamino)propyl]phenyl-2-phenyl-2-propen-1-one.

* * * * *